United States Patent [19]

Yabusaki

[11] Patent Number: 4,459,362
[45] Date of Patent: * Jul. 10, 1984

[54] IMMUNOASSAY OF PHOSPHOLIPID, SUCH AS PHOSPHATIDYL CHOLINE, IN FLUIDS SUCH AS AMNIOTIC

[75] Inventor: Kenichi K. Yabusaki, Albany, Calif.

[73] Assignee: Hana Biologics, Inc., Emeryville, Calif.

[*] Notice: The portion of the term of this patent subsequent to Jun. 14, 2000 has been disclaimed.

[21] Appl. No.: 426,614

[22] Filed: Sep. 29, 1982

Related U.S. Application Data

[63] Continuation-in-part of Ser. No. 344,930, Feb. 2, 1982, Pat. No. 4,388,412.

[51] Int. Cl.$^3$ .................. G01N 33/54; G01N 33/92
[52] U.S. Cl. .................. 436/536; 436/63; 436/71; 436/543; 436/547; 436/811; 436/815
[58] Field of Search .................. 436/536, 63, 71, 543, 436/547, 811, 815

[56] References Cited

U.S. PATENT DOCUMENTS

| | | |
|---|---|---|
| 4,233,032 | 11/1980 | Statland . |
| 4,257,771 | 3/1981 | Yee . |
| 4,290,772 | 9/1981 | Frey ........................ 436/17 |
| 4,292,041 | 9/1981 | Fullerton . |
| 4,370,311 | 1/1983 | Ilekis . |

OTHER PUBLICATIONS

Chemical Abstracts, 92:142867m, (1980).
Chemical Abstracts, 93:128400t, 112185r and 112186s, (1980).
I. Inoue et al., Biochimica et Biophysica Acta, vol. 144, No. 2, issued Oct. 2, 1967, "Immunochemical Studies of Phospholipids. III Production of Antibody to Cardiolipin", pp. 409–414.
Gluck, L., et al., Am. J. Obstet. Gynecol., 109:3, 440–445, 1971.
Hallman, M. and Gluck, L., J. Lipid Res., 17, 257–262, 1976.
Hallman, M., et al., Am. J. Obstet. Gynecol., 125, 613–617, 1976.
Cunningham, M D., et al., Am. J. Obstet. Gynecol., 131, 719–724, 1978.
Freer, D. E., et al., Clin. Chem., 25, 960–968, 1978.
Bustos, R., et al., Am. J. Obstet. Gynecol., 133, 399–903, 1979.
Kulovich, M. V., et al., Am. J. Obstet. Gynecol., 135, 57–63, 1979.
Kulovich, M. V. and Gluch, L., Am. J. Obstet. Gynecol., 135, 64–70, 1979.
Tsai, M. Y., and Marchall, J. G., Clin. Chem., 25, 682–685, 1979.
Bent, A. E., et al., Am. J. Obstet. Gynecol., 139, 259–263, 1981.
Tsao, F. H. C., and Zachman, R. D., Clin. Chem. Acta, 118, 109–120, 1982.
Freer, D. E., and Statland, B. E., Clin. Chem., 27, 1629–1641, 1981.
Bligh, E. G., and Dyer, W. J., Can. J. Biochem. Physiol., 37, 911–917, 1959.
Wells, M. A., and Hanahan, D. J., Biochemistry, 8, 414–424, 1969.
Dittmer, J. C. and Wells, M. A., *Methods in Enzymology*, XIV Lipids, J. M. Lowenstein, Ed., Academic Press, N.Y., 1969, pp. 482–530.
Inoue, K. and Nojima, S., Biochem. Biophys. Acta., 144, 409–414, 1967.
Harris A., Rosenberg, A. A. and Riedel, L. M., J. Ven. Dis. Inform., 27, 169–174, Jul. 1946.
Garvey, J. S., Cremer, N. E. and Sussdorf, D. H., Methods in Immunology, 3rd Ed., W. A. Benjamin, Inc., Mass., 1977, pp. 218–219.
Maltaner, E. and Maltaner, F., Immunol., 51, 195–214, 1945.
Gotelli, G. R., et al., Clin. Chem., 24:7, 1144–1146, 1978.
Gluck, L., Clin. Chem. 23:1107, 1977.
Ip, M. P. C. et al., Clin. Chem., 23:35, 1977.
Mackenna, J., et al., Obstet. & Gynecol., 57:4, 493–495, 1981.
Cavalieri, R. et al., Amer. J. Obstet. Gynecol., 141:6, 652–656, 1981.
Freer, D. E. et al., Clin. Chem., 25:6, 960–968, 1979.
Jangalwala, F. B. et al., Biochem. J., 155, 55–60, 1976.
Anaokar, S. et al., Clin. Chem., 25:1, 103–107, 1978.
Nelson, G. H., Am. J. Obstet. Gynecol., 115:7, 933–941, 1973.
Jimenez, J. M. et al., Gynecol. Invest., 5:245–251, 1974.
Duck-Chong, C. G. et al., Clin. Chem., 26/6, 766–769, 1980.
Tiwary, C. M., and Goldkrand, J. W., Obstet. & Gynecol., 48:2, 191–194, 1976.
Clements, J. A. et al., N. Eng. J. Med., 286–20, 1077–1081, 1972.
Shinitzky, M. et al., Br. J. Obstet. Gynecol., 83, 838–844, 1976.
Sbarra, A. J. et al., Obstet. Gynecol., 48:5, 613–615, 1976.
Sing, E. J., Am. J. Obstet. Gynecol., 136:2, 228–229, 1980.

*Primary Examiner*—Sidney Marantz
*Attorney, Agent, or Firm*—Limbach, Limbach & Sutton

[57] ABSTRACT

An immunologic assay for determining the presence of one or more phospholipids in a biological fluid. The method includes adding an ethanolic solution of diacylphosphatidylcholine or alkyltrimethylammonium halide and cholesterol to the biological fluid forming a macromolecular aggregate complex suspension. To the macromolecular aggregate complex solution is then added either an additional quantity of the biological fluid or a buffer reagent. The product of the reaction is then added to antibody molecules to the phospholipid and examined to determine the presence of the phospholipids.

The method is particularly useful in determining the presence of phosphatidylglycerol in a sample of amniotic fluid.

18 Claims, No Drawings

IMMUNOASSAY OF PHOSPHOLIPID, SUCH AS PHOSPHATIDYL CHOLINE, IN FLUIDS SUCH AS AMNIOTIC

RELATED APPLICATION

This application is a continuation-in-part of U.S. Application Ser. No. 344,930, filed Feb. 2, 1982, now U.S. Pat. No. 4,388,412 entitled "ANALYSES OF BIOLOGICAL FLUIDS".

BACKGROUND OF THE INVENTION

It has been found quite useful to know the levels of phospholipids in biological fluids, generally. For example, phospholipids, particularly lecithin, are found in various biological membranes. Further, the phospholipid phosphatidylglycerol, as more fully described below, is found in amniotic fluid and can be used as an indicator of the lung maturity of the fetus. Other phospholipids besides lecithin (phosphatidylcholine) and phosphatidylglycerol which can be detected employing the method disclosed herein are, for example, phosphatidylinositol, phosphatidylserine and phosphatidylethanolamine. Although the present invention will be described in terms of its most preferred embodiment, that is, the determination of phosphatidylglycerol levels in amniotic fluid, the present invention can be used to determine the levels of any of the above-recited phospholipids in biological fluids, generally.

Proper functioning of the pulmonary system is essential for the fetus to survive in an extrauterine environment. Infants born with respiratory difficulties are said to have respiratory distress syndrome (RDS). The primary etiological defect in respiratory distress syndrome is a deficiency of surfactant, a complex mixture of lipids, proteins, and carbohydrates essential to the proper functioning of the mature lung. In the mature lung, phospholipids comprise 90–95% of the lipids. The major surface active phospholipid found in the surfactant is dipalmitoyllecithin. The second major surface active phospholipid is phosphatidylglycerol.

The most direct means of prenatally assessing fetal pulmonary maturity is measuring the production of lung surfactant phospholipids such as phosphatidylcholine (lecithin) and phosphatidylglycerol.

It has been determined that as pregnancy progresses, the sphingomyelin level in the surfactant remains relatively constant, while the lecithin level continues to increase, showing a very sharp increase after the 35th week of gestation. In the mature lung, lecithin comprises at least 50% of the total surfactant lipids. The constant level of sphingomyelin provides an internal reference for comparison with the surface active lecithin, thus providing the basis for the lecithin to sphingomyelin ratio (L/S) test developed by Gluck et al. as described in Am. J. Obstet. Gynecol., 109: 440 (1971).

Recent studies by Hallman et al. reported in Am. J. Gynecol., 125: 613 (1977), Tsai et al., Clin. Chem., 25: 682 (1979), Gotelli et al., Clin. Chem., 24: 1144 (1978), and Cunningham et al., Am. J. Obstet. Gynecol., 131: 719 (1978), indicate that measurement of phosphatidylglycerol may be of value in determining fetal pulmonary maturity. As alluded to previously, phosphatidylglycerol appears during the 35th–38th gestational week and has a good linear correlation with the L/S ratio. More to the point, Gluck, as reported in Clin. Chem., 23: 1107 (1977), points out that only after the appearance of phosphatidylglycerol in amniotic fluid is delivery safe in diabetic mothers. It was also discovered that the presence of blood or meconium in amniotic fluid affects the lecithin to sphingomyelin (L/S) ratio but not the level of phosphatidylglycerol. Although the L/S ratio test has gained wide acceptance as the most reliable prognostic index of fetal pulmonary maturity in most pregnancies, the results must be interpreted with caution for certain maternal complications such as diabetes mellitus, hypertension, severe anemia and intrinsic renal disease, can adversely affect the L/S ratio readings.

It was therefore found desirable to find alternative methods of assessing fetal pulmonary maturity, which are relatively fast, specific and require a minimum amount of skill, experience and sophisticated instrumentation to gain results with high precision and accuracy. It was the development of these alternative methods which led to the present invention for the determination of the presence of phospholipids in a biological fluid. The prior art has used biochemical quantitation and biophysical measurements as techniques for evaluating amniotic fluid surfactant. All of the prior art methods, however, suffer from either being overly time consuming and tedious, and requiring skill and expertise to obtain reasonably high precision, and requiring the use of hazardous chemicals and highly sophisticated and expensive instrumentation or in providing methods which are simply non-specific. The present invention provides a method exhibiting none of these drawbacks.

SUMMARY OF THE INVENTION

The present invention embraces an immunologic assay method for determining the presence of a phospholipid in a biological fluid. By the addition of a defined mixture of a diacylphosphatidylcholine such as, for example, hen egg yolk lecithins or an alkyltrimethylammonium halide such as, for example, hexadecyltrimethylammonium bromide, and cholesterol to the biological fluid, phospholipids present in the biological fluid are incorporated into macromolecular aggregate complexes of lecithin, or alkyltrimethylammonium halide, cholesterol and other biological fluid components. By employing receptor molecules specific for the phospholipids being measured, a sensitive and rapid technique is provided for assessing for the level of specific phospholipids. By combining both the phospholipid, the diacylphosphatidylcholine or alkyltrimethylammonium halide and cholesterol and biological fluid components in the form of the macromolecular aggregate complexes with specific receptors for the phospholipids in a buffered aqueous medium, an agglutination reaction results. The technique is particularly advantageous in determining the presence of phosphatidylglycerol in amniotic fluid.

DETAILED DESCRIPTION OF THE INVENTION

In carrying out the subject method, a known amount of ethanolic solution of cholesterol and a diacylphosphatidylcholine such as hen egg yolk lecithins or a known amount of ethanolic solution of cholesterol and an alkyltrimethylammonium halide such as hexadecyltrimethylammonium bromide are added to a known volume of biological fluid. When amniotic fluid is used as a biological fluid, it is first centrifuged and the ethanolic solution added to a fraction of the centrifugate. After mixing, an additional known volume of centrifuged amniotic fluid or a Buffer Reagent containing a known amount of diacylphosphatidylcholines (Lecithins) or alkyltrimethylammonium halide is added and if phosphatidylglycerol is present in the amniotic fluid sample, macromolecular aggregates are formed of the diacylphosphatidylcholine or alkyltrimethylammonium halide, cholesterol, phosphatidylglycerol and other amniotic fluid components. The addition of a known volume of the phosphatidylglycerol macromolecular aggregate complex solution to a known amount of antibody molecules to phosphatidylglycerol in a buffered aqueous medium results in an agglutination reaction indicating the presence of phosphatidylglycerol.

The above-described method can be carried out using relatively small quantities of biological fluid. For example, the phosphatidylglycerol level can be determined in amniotic fluid obtained by transabdominal amniocentesis producing less than 3.0 ml amniotic fluid. In fact, the above-described method can be carried out employing usually no more than 1 ml of the biological fluid.

The ethanolic solution of cholesterol and diacylphosphatidylcholine will contain cholesterol in the range of approximately 0.5 to 12 mg/ml, more usually 5 to 10 mg/ml and most preferably 8 to 9 mg/ml and diacylphosphatidylcholines in the range of 0.05 to 10 mg/ml, more usually 0.5 to 3 mg/ml and most preferably approximately 1.5 to 2.0 mg/ml.

The ethanolic solution of cholesterol and alkyltrimethylammonium halide will contain cholesterol in the range of approximately 0.5 to 12 mg/ml, more usually 5 to 10 mg/ml and most preferably 8 to 9 mg/ml and alkyltrimethylammonium halide in the range of 0.1 to 5 mg/ml, more usually 0.5 to 3 mg/ml, and most preferably approximately 1 to 2 mg/ml.

The Buffer Reagent contains phosphate buffered in the range of approximately pH 4 to 8, more usually 5 to 7 and most preferably 6. The concentration of buffer will generally be in the range of approximately 0.001 to 0.5 Molar, more usually in the range of approximately 0.005 to 0.1 Molar and preferably approximately 0.0175 to 0.05 Molar. The Buffer Reagent will also contain diacylphosphatidylcholines or alkyltrimethylammonium halide in the range of approximately 1 to 200 mg/liter, more usually in the range of 10 to 100 mg/liter and most preferably 40 to 80 mg/liter.

The antibodies to phosphatidylglycerol will be buffered in the range of approximately pH 5 to 10, more usually approximately 5.5 to 8.0 and most preferably approximately 6.0 to 7.0. Various buffers may be used such as Tris, phosphate and the like, while the preferred buffer is the phosphate. The concentration of buffer will generally be in the range of approximately 0.001 to 0.5 Molar, more usually in the range of approximately 0.005 to 0.1 Molar and preferably approximately 0.0175 to 0.05 Molar.

Other additives may also be in the assay medium which are employed for preserving or protecting individual components or reagents or for aiding the performance characteristics of the assay. Particularly, sodium chloride can be employed in amounts of approximately 0.01 to 5 weight percent, more usually approximately 0.05 to 2.0 weight percent and preferably approximately 0.5 to 1.0 weight percent.

The quantity of diacylphosphatidylcholines or alkyltrimethylammonium halides and cholesterol which are added to the biological fluid must be added in a quantity large enough to allow the distribution of the phospholipids if present in the biological fluid sample to distribute into macromolecular aggregates such that the antibody molecules to the phospholipids can effectively bind to the phospholipid molecules. The amount of antibody to phospholipid which is employed will vary and be chosen to provide the desired agglutination reaction.

EXAMPLE

A. Preparation of Phosphatidylglycerol Immunogen Complex

Approximately 45 mg L-phosphatidyl-DL-glycerol (0.058 mMole) in chloroform and approximately 270 mg hen egg yolk lecithins (0.34 mMole) in methanol were dried under a stream of nitrogen gas and dissolved in approximately 10 ml of absolute ethanol and placed in a 500 ml Erlenmeyer flask. To the L-phosphatidyl-DL-glycerol-lecithin solution is added 1.35 grams of cholesterol which was dissolved in approximately 135 ml of absolute ethanol.

To the above mixture was added 145 ml of 0.0175 Molar sodium phosphate buffer, pH 6.0. This resulted in the formation of a white colloidal emulsion which was allowed to stir for 15 minutes at room temperature and then centrifuged at approximately 13,000×g for 10 minutes at 4° C. The resulting pellet was resuspended in a 2% methylated bovine serum albumin solution in 0.0175 Molar sodium phosphate buffer, pH 6.0. The resulting L-phosphatidyl-DL-glycerol:Lecithin:cholesterol: m-BSA complex was left overnight at 4° C.

Four milliliter aliquots of the L-phosphatidyl-DL-glycerol-immunogen solution was lyophilized and the resulting powder stored at −20° C.

B. Anti-phosphatidylglycerol Antibodies

The lyophilized phosphatidylglycerol-immunogen complex prepared above was suspended in 4 ml of sterile distilled water by vortexing and thorough mixing such that the final concentration of the immunogenic protein was 20 mg/ml.

Approximately 0.5 ml aliquot of the above phosphatidylglycerol-immunogen complex was injected intravenously per rabbit every two days for a period of three successive weeks. The total dosage was about 4.5 ml at 20 mg immunogenic protein per milliliter. After the last injection, a period of 5 to 7 days was allowed to pass and the rabbit bled by heart puncture. When the desired amount of blood was collected (about 20–30 ml) the blood was allowed to clot and the clot removed. The remaining solution was centrifuged at 2,000 RPM for 10 minutes. The serum was collected free of loose red blood cells resulting in collection of the anti-phosphatidylglycerol antiserum.

Subsequently, rabbits which were found to be immune were subjected once a month to the following injection protocol. Rabbits were injected intravenously once every two days over a period of one week with 0.5 ml per injection of the phosphatidylglycerol-immunogen described above and bled via heart puncture 5 to 7 days after the last injection. The blood was collected and processed as described above.

C. Purification of Anti-Phosphatidylglycerol Antiserum

To a known volume of rabbit serum containing a high titer of anti-phosphatidylglycerol activity is slowly added half of the above volume of a freshly prepared saturated solution of ammonium sulfate which has been adjusted to a pH of approximately 7.8 with 2 Normal NaOH. This solution was stirred at room temperature for approximately two hours and then centrifuged at 1400×g for 30 minutes at approximately 4° C. The pellet was dissolved in a minimum of 0.85% NaCl and then dialyzed against 0.0175 Molar sodium phosphate buffer, pH 6.5, containing 0.85% NaCl for two days at 4° C. with several changes of the above mentioned buffer. The contents of the dialysis bag were centrifuged at 1400×g for 30 minutes, resulting in an IgG rich supernatant.

The above-derived IgG fraction was then cleansed of interfering anti-cholesterol antibodies by the following procedure. To approximately 6.8 ml of Buffer Reagent in a sterile 25 ml flask under magnetic stirring is added dropwise 8.8 ml of Lecithin-Cholesterol Reagent (Reagent A). The resultant emulsion is stirred for an additional 2 minutes then this emulsion added to 160 ml of IgG fraction in a sterile 250 ml flask. This mixture is allowed to stir gently for 5 minutes then allowed to stand at room temperature for 4 hours with a gentle 2 minute mixing once each hour and stored at 2°–4° C. overnite. After a gentle 2 minute mixing, the emulsion is centrifuged at 10,000×g for 10 minutes at 4° C. The resultant supernatant is termed anti-Phosphatidylglycerol IgG (anti-PG IgG). The antibody solution was diluted appropriately to give the desired agglutination reaction with standardized control solutions containing known amounts of phosphatidylglycerol. The dilutant for the anti-phosphatidylglycerol antibodies was 0.0175 Molar sodium phosphate buffer, pH 6.0 containing 1.0% NaCl.

D. Preparation of the Lecithin-Cholesterol Reagent

Approximately 90 mg of cholesterol was dissolved in approximately 9.5 ml of absolute ethanol by heating the solution under a stream of hot tap water. After cooling, the final volume was made to 10.0 ml with the addition of 15 mg of diacylphosphatidylcholines in approximately 0.5 ml of absolute ethanol.

E. Preparation of the Hexadecyltrimethylammonium Bromide-Cholesterol Reagent

Approximately 90 mg of cholesterol was dissolved in approximately 9.5 ml of absolute ethanol by heating the solution under a stream of hot tap water. After cooling, the final volume was made to 10.0 ml with the addition of 10 mg of hexadecyltrimethylammonium bromide in approximately 0.5 ml of absolute ethanol.

F. Preparation of the Buffer Reagent

Approximately 0.9 ml of an ethanolic solution containing 20 mg/ml of hen egg yolk lecithins or 20 mg/ml of hexadecyltrimethylammonium bromide are added to 440 ml of a 0.0175 Molar sodium phosphate buffer, pH 6.0, solution under magnetic stirring. After the last addition of the lecithins or hexadecyltrimethylammonium bromide, the mixture was allowed to stir for an additional 2 minutes.

G. (I) Agglutination Test for Phosphatidylglycerol Reagents (Embodiment I)

1. a. Lecithin-cholesterol reagent approximately 0.15% lecithin, approximately 0.9% cholesterol (Reagent A) or b. Hexadecyltrimethylammonium bromide-cholesterol reagent approximately 0.1% hexadecyltrimethylammonium bromide, approximately 0.9% cholesterol (Reagent A)

2. Anti-phosphatidylglycerol antibody solution (Reagent B)

3. Negative, weak positive, and strong positive control solutions.

The Negative Control contains in 0.0175 Molar sodium phosphate buffer, pH 6.0, hen egg yolk lecithins or hexadecyltrimethylammonium bromide in the range of approximately 1 to 200 mg/liter, more usually 10 to 100 mg/liter and most preferably approximately 40 to 80 mg/liter.

The Weak Positive Control contains in 0.0175 Molar sodium phosphate buffer, pH 6.0, approximately 2 mg/liter phosphatidylglycerol and hen egg yolk lecithins or hexadecyltrimethylammonium bromide in the range of approximately 1 to 200 mg/liter, more usually 10 to 100 mg/liter and most preferably approximately 40 to 80 mg/liter.

The Strong Positive Control contains in 0.0175 Molar sodium phosphate buffer, pH 6.0, approximately 4 mg/liter phosphatidylglycerol and hen egg yolk lecithins or hexadecyltrimethylammonium bromide in the range of approximately 1 to 200 mg/liter, more usually 10 to 100 mg/liter and most preferably approximately 40 to 80 mg/liter.

4. Buffer Reagent approximately 40 mg/liter hen egg yolk lecithins or 40 mg/liter hexadecyltrimethylammonium bromide in 0.0175 Molar sodium phosphate buffer, pH 6.0.

G. (II) Agglutination Test for Phosphatidylglycerol Reagents (Embodiment II)

1. a. Lecithin-cholesterol reagent: approximately 0.15% lecithin, approximately 0.9% cholesterol (Reagent A) or b. Hexadecyltrimethylammonium bromide-cholesterol reagent: approximately 0.1% hexadecyltrimethylammonium bromide approximately 0.9% cholesterol (Reagent A).

2. Antiphosphatidylglycerol antibody solution (Reagent B).

3. Negative, weak positive and strong positive control solutions as in Embodiment I.

4. Supernatant from centrifuged amniotic fluid.

A suitably sized test tube was appropriately marked for each sample and control sample to be assayed. To each respective test tube was added supernatant from a centrifuged sample of amniotic fluid and negative, weak positive, or strong positive samples in the ranges of approximately 0.005 to 1.0 ml, more usually 0.01 to 0.5 ml and most preferably approximately 0.025 to 0.2 ml. To each test tube was then added dropwise when possible Reagent A in the ranges of approximately 0.005 to 1.5 ml or more usually approximately 0.01 to 0.5 ml and most preferably approximately 0.025 to 0.2 ml, while mixing the contents of the tube thoroughly to provide for thorough mixing by tapping the test tube with a finger. Then to each test tube was added additional supernatant from a centrifuged amniotic fluid sample or Buffer Reagent in the range of approximately 0.045 to 10 ml, more usually approximately 0.2 to 5 ml, and most preferably approximately 0.3 to 1. ml.

Approximately 0.005 to 0.1 ml, more usually approximately 0.01 to 0.75 ml and most preferably approximately 0.025 to 0.05 ml of the anti-PG solution (Reagent B) was pipetted onto the centers of separate test rings of an agglutination slide for each sample and control to be assayed. This was followed by the pipetting of each negative, weak positive and strong positive control samples and amniotic fluid sample macromolecular aggregate suspensions onto the centers of the anti-PG droplets in the centers of the separate test rings of the agglutination slide in the ranges of approximately 0.002 to 0.05 ml, more usually approximately 0.005 to 0.04 ml and most preferably approximately 0.01 to 0.03 ml. Each macromolecular aggregate suspension was mixed thoroughly before an aliquot was removed via pipetting. The agglutination slide was then placed on the platform of a serological rotor and rotated at a constant speed of, for example, approximately 60 revolutions per minute for approximately ten minutes. The slide was then placed on a mirror and the droplets in each test ring examined. A positive reaction for the presence of phosphatidylglycerol is indicated by relatively large agglutinated particles with a distinctly clear background as in the rings containing the weak positive and strong positive control samples. A negative reaction has a slightly grainy appearance and the absence of a distinctly clear background.

Although the above recited example is particularly directed toward the determination of the presence of phosphatidylglycerol in a sample of amniotic fluid, the technique shown and described is equally valuable in determining the presence of phospholipids, generally, in a biological fluid.

What is claimed is:

1. A method of determining the presence of a phospholipid in a biological fluid comprising:
   A. adding an ethanolic solution of cholesterol and a member selected from the group consisting of diacylphosphatidylcholine and an alkyltrimethylammonium halide to the biological fluid forming a macromolecular aggregate complex suspension;
   B. adding the macromolecular aggregate complex solution to antibody molecules to the phospholipid in an aqueous buffered medium causing an agglutination reaction; and
   C. adding additional biological fluid in an amount as to enable a determination of the presence of the phospholipid.

2. A method of determining the presence of a phospholipid in a biological fluid comprising:
   A. adding an ethanolic solution of cholesterol and a member selected from the group consisting of diacylphosphatidylcholine and an alkyltrimethylammonium halide to the biological fluid forming a macromolecular aggregate complex suspension;
   B. adding the macromolecular aggregate complex solution to antibody molecules to the phospholipid in an aqueous buffered medium causing an agglutination reaction; and
   C. adding buffer reagent comprising a buffer and a member selected from the group consisting of diacylphosphatidylcholine and alkyltrimethylammonium halide in an amount as to enable a determination of the presence of the phospholipid.

3. The method of claims 1 or 2 wherein the phospholipid is a member from the group consisting of phosphatidylcholine, phosphatidylinositol, phosphatidylserine, phosphatidylethanolamine and phosphatidylglycerol.

4. The method of claims 1 or 2 wherein the biological fluid comprises amniotic fluid.

5. The method of claim 4 wherein the phospholipid comprises phosphatidylglycerol.

6. The method of claims 1 or 2 wherein sufficient diacylphosphatidylcholine and cholesterol are added to the biological fluid such that the phospholipid-containing macromolecular aggregates can be bound to the antibody molecules.

7. The method of claims 1 or 2 wherein sufficient alkyltrimethylammonium halide and cholesterol are added to the biological fluid such that the phospholipid containing macromolecular aggregates can be bound to the antibody molecules.

8. The method of claim 2 wherein the buffer comprises sodium phosphate.

9. The method of claim 2 wherein the pH of the buffer reagent is approximately 5 to 7.

10. The method of claim 2 wherein the buffer reagent in the biological fluid containing solution is in a concentration of approximately 0.001 to 0.5 molar.

11. The method of claim 2 wherein the member selected from the group consisting of diacylphosphatidylcholine and alkyltrimethylammonium halide is present in the buffer reagent in a concentration of 1 to 200 mg/l.

12. The method of claims 1 or 2 wherein the alkyltrimethylammonium halide is hexadecyltrimethylammonium bromide.

13. A method of determining the presence of phosphatidylglycerol in a sample of amniotic fluid comprising:
   A. adding an ethanolic solution of cholesterol and a member selected from the group consisting of diacylphosphatidylcholine and alkyltrimethylammonium halide to a sample of amniotic fluid forming macromolecular aggregates of cholesterol, phosphatidylglycerol and a member selected from the group consisting of diacylphosphatidylcholine and alkyltrimethylammonium halide;
   B. adding additional amniotic fluid in an amount as to enable a determination of the presence of the phosphatidylglycerol; and
   C. forming an agglutination reaction by adding the phosphatidylglycerol macromolecular aggregate complex containing suspension to a known quantity of antibody molecules to the phosphatidylglycerol in a buffered aqueous medium.

14. A method of determining the presence of phosphatidylglycerol in a sample of amniotic fluid comprising:
   A. adding an ethanolic solution of cholesterol and a member selected from the group consisting of diacylphosphatidylcholine and alkyltrimethylammonium halide to a sample of amniotic fluid forming macromolecular aggregates of cholesterol, phosphatidylglycerol and a member selected from the group consisting of diacylphosphatidylcholine and alkyltrimethylammonium halide;
   B. adding buffer reagent comprising a buffer and a member selected from the group consisting of diacylphosphatidylcholine and alkyltrimethylammonium halide in an amount as to enable a determination of the presence of the phosphatidylglycerol; and
   C. forming an agglutination reaction by adding the phosphatidylglycerol macromolecular aggregate complex containing suspension to a known quantity of antibody molecules to the phosphatidylglycerol in a buffered aqueous medium.

15. The method of claims 1, 2, 13 or 14 wherein the complex solution further comprises sodium chloride.

16. The method of claim 15 wherein the sodium chloride is present in an amount between approximately 0.05 to 2.0 weight percent.

17. The method of claims 1, 2, 13 or 14 wherein the diacylphosphatidylcholine comprises hen egg yolk lecithin.

18. The method of claims 13 or 14 wherein the alkyltrimethylammonium halide is hexadecyltrimethylammonium bromide.

* * * * *